United States Patent [19]

Richter et al.

[11] 4,051,166

[45] Sept. 27, 1977

[54] ARALIPHATIC DIISOCYANATES

[75] Inventors: Reinhard H. Richter, North Haven; Benjamin W. Tucker, Bethany; Henri Ulrich, Northford, all of Conn.

[73] Assignee: The Upjohn Company, Kalamazoo, Mich.

[21] Appl. No.: 693,793

[22] Filed: June 8, 1976

[51] Int. Cl.² ........................................... C07C 119/048
[52] U.S. Cl. ....................... 260/453 AR; 260/2.5 AT; 260/77.5 AT; 260/465 F; 260/570.7
[58] Field of Search ................................. 260/453 AR

[56] References Cited

U.S. PATENT DOCUMENTS

| | | | |
|---|---|---|---|
| 2,360,210 | 10/1944 | Dickey et al. | 260/453 X |
| 3,198,821 | 8/1965 | Brotherton et al. | 260/454 |
| 3,267,122 | 8/1966 | Lehmann et al. | 260/453 |
| 3,342,846 | 9/1967 | Cometti et al. | 260/454 |
| 3,884,951 | 5/1975 | Oswald | 260/453 |

*Primary Examiner*—Dolph H. Torrence
*Attorney, Agent, or Firm*—James S. Rose; Denis A. Firth

[57] ABSTRACT

Novel araliphatic diisocyanates having the formula $$OCN(CH_2)_3 \, OArX(CH_2)_3 \, NCO$$

are disclosed wherein X is oxygen or a single bond and Ar is an arylene radical. The araliphatic diisocyanates are prepared from well known and readily obtainable starting materials. When X represents a single bond, the starting material is a monohydric phenol wherein a C-alkylation reaction followed by an O-alkylation reaction with acrylonitrile provides an intermediate dipropionitrile which is converted to the diisocyanate via phosgenation of the corresponding diamine. When X represents oxygen, the starting material is a dihydric phenol wherein O-alkylation with acrylonitrile provides the dipropionitrile which in turn is converted to the diisocyanate via the phosgenation of the corresponding diamine. The diisocyanates find particular utility in the preparation of color and light stable polyurethane products.

9 Claims, No Drawings

4,051,166

ARALIPHATIC DIISOCYANATES

BACKGROUND OF THE INVENTION

1. Field of the Invention

This invention relates to the preparation of organic isocyanates, and, more particularly, is concerned with the preparation of novel araliphatic diisocyanates.

2. Description of the Prior Art

Organic diisocyanates find particular utility in the preparation of polyurethane plastics, particularly elastomeric polyurethanes used in the production of fibers, films, and various cast and formed articles. The art has long recognized the problems which arise with respect to the color stability, and, even mechanical properties, upon ageing, of those urethanes containing aromatic diurethane linkages. For example, a clear colorless polymer when exposed to the action of sunlight, or equivalent ultraviolet irradiation, will change to yellow then to amber, and on extensive exposure even to a brown. Mechanical property losses generally occur concurrently with the color changes.

In contrast, those urethanes prepared from aliphatic, cycloaliphatic, or araliphatic diisocyanates, generally speaking, provide for enhanced polyurethane stability, especially in regard to color stability as well as mechanical property retention. This phenomenon is widely recognized and amply documented by C. S. Schollenberger and F. D. Stewart, J. Elastoplastics 4, 294 (1972).

We have now found a novel class of araliphatic diisocyanates which are particularly useful for the preparation of light stable polyurethane polymers and which are easily prepared from readily available and economically attractive starting materials.

Related aryl(isothiocyanatoalkoxylates) have been reported as useful for fungicides and anthelmintics; see U.S. Pat. Nos. 3,198,821 and 3,342,846. However, the prior art has not recognized the analogous oxygen compositions for their ability to provide color stable polyurethane products which is an object of the present invention.

SUMMARY OF THE INVENTION

This invention comprises an araliphatic diisocyanate having the formula

OCN(CH$_2$)$_3$OArX(CH$_2$)$_3$NCO   I wherein X is oxygen or a single bond and Ar is an arylene radical.

The invention also comprises processes for the preparation of the novel araliphatic diisocyanates.

The invention also comprises the novel polyurethane compounds prepared from the novel araliphatic diisocyanates.

The term "arylene" means a radical obtained by removing two nuclear hydrogen atoms from an aromatic hydrocarbon, and is inclusive of phenylene, tolylene, naphthylene, diphenylylene, and radicals having the formula

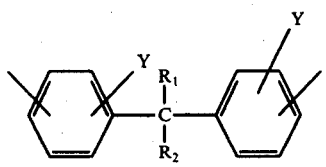

wherein R$_1$ and R$_2$ each represent a moiety selected from the class consisting of hydrogen and alkyl having from 1 to 4 carbon atoms inclusive, and Y is selected from the group consisting of hydrogen, alkyl from 1 to 4 carbon atoms, and alkoxy from 1 to 4 carbon atoms. Illustrative of alkyl from 1 to 4 carbon atoms are methyl, ethyl, propyl, butyl and isomeric forms thereof. Illustrative of alkoxy from 1 to 4 carbon atoms are methoxy, ethoxy, propoxy, butoxy and isomeric forms thereof.

DETAILED DESCRIPTION OF THE INVENTION

The novel diisocyanates of the present invention having the formula (I) set forth above belong to the class of araliphatic diisocyanates wherein at least one —NCO group is linked to the aromatic hydrocarbon group Ar through the 3-isocyanatopropoxy group, while the second —NCO group is linked to the aromatic hydrocarbon either by a 3-isocyanatopropoxy (when x represents oxygen), or a 3-isocyanatopropyl group (when x represents a single bond).

These two substituent groups can be in ortho-, meta-, or para- relationship to each other when substituted on the same aromatic ring of the arylene hydrocarbon. Conversely, when there is more than one aromatic ring in the arylene hydrocarbon, both groups are not limited to one aromatic ring but may take up isomer positions which include distribution in different aromatic rings.

Illustratively, the arylene radical having the definition hereinabove set forth includes ortho-, meta-, and para- phenylene, 2,4-tolylene, 2,5-tolylene, 1,4-naphthylene, 1,5-naphthylene, 4,4'-biphenylene, 4,4'-isopropylidenediphenylene, 4,4'-methylenediphenylene, and the like. A preferred group of arylene radicals consists of ortho-, meta-, and para- phenylene, and 4,4'-isopropylidenediphenylene.

Included in the broad scope of the present invention are the following types of araliphatic diisocyanates.

A. A (3-isocyanatopropoxy)-(3-isocyanatopropyl) arylene compound having the formula OCN(CH$_2$)$_3$OAr(CH$_2$)$_3$NCO   II wherein Ar has the definition set forth above. Illustrative of members of the diisocyanates of formula (II) are:

1-(3-isocyanatopropoxy)-4-(3-isocyanatopropyl)benzene;
1-(3-isocyanatopropoxy)-4-(3-isocyanatopropyl)-2-methylbenzene;
1-(3-isocyanatopropoxy)-4-(3-isocyanatopropyl)-3-methylbenzene;
1-(3-isocyanatopropoxy)-2-(3-isocyanatopropyl)-4-methylbenzene;
1-(3-isocyanatopropoxy)-4-(3-isocyanatopropyl) naphthalene; and
1-(3-isocyanatopropyl)-2-(3-isocyanatopropoxy) naphthalene A preferred member of the diisocyanates of formula II is 1(3-isocyanatopropoxy)-4-(3-isocyanatopropyl)-benzene.

B. A bis(3-isocyanatopropoxy)arylene compound having the formula:

OCN(CH$_2$)$_3$ OArO(CH$_2$)$_3$ NCO   III wherein Ar has the definition set forth above.

Illustrative of members of the diisocyanates of formula (III) are:

1,4-bis(3-isocyanatopropoxy)benzene;
1,3-bis(3-isocyanatopropoxy)benzene;
1,2-bis(3-isocyanatopropoxy)benzene;
1,3-bis(3-isocyanatopropoxy)naphthalene;
1,4-bis(3-isocyanatopropoxy)naphthalene;
1,5-bis(3-isocyanatopropoxy)naphthalene;
2,3-bis(3-isocyanatopropoxy)naphthalene;
2,7-bis(3-isocyanatopropoxy)naphthalene;
4,4'-bis(3-isocyanatopropoxy)-3,3'-dimethyl-biphenyl; and
2,2-bis [p(3-isocyanatopropoxy)phenyl]propane.

A preferred group of araliphatic diisocyanates of formula (III) consists of 1,4-bis(3-isocyanatopropoxy)benzene, 1,3-bis(3-isocyanatopropoxy)benzene, 1,2-bis(3-isocyanato-propoxy)benzene, and 2,2-bis[p(3-isocyanatopropoxy)phenyl]propane.

The araliphatic diisocyanates of formula (I) above are prepared by beginning with one or the other of the following Schemes A and B below wherein a phenolic compound (IV) is reacted with sufficient acrylonitrile (V) to cyanoethylate a phenolic hydroxyl position and an arylene ring position, or two phenolic hydroxyls, depending on whether X represents a single bond or an oxygen.

Scheme A. When X represents a single bond:

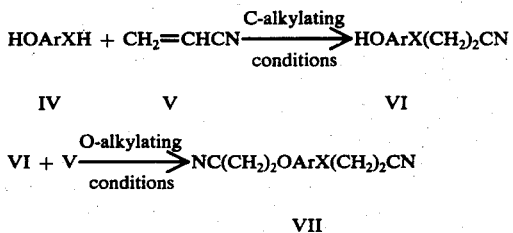

Scheme B. When X represents oxygen:

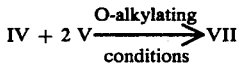

It will be readily apparent to those skilled in the art that the starting material (IV) of Scheme A represents a monohydric phenol wherein X is a single bond linking hydrogen to the aromatic hydrocarbon. It is preferable to carry out the C-alkylation reaction to form (VI) first, followed by the cyanoethylation of (VI) under O-alkylating conditions to form the dipropionitrile derivative (VII). Otherwise the reverse procedure could result in cleavage of the alkoxy ether linkage under the acidic conditions of the C-alkylation reaction.

The C-alkylation, or ring cyanoethylation reaction is readily performed by bringing together the monohydric phenol and the acrylonitrile at elevated temperatures and in the presence of an equimolar amount of a Lewis acid catalyst using methods which are well known and described, for example, in J. Org. Chem. 22, 1264 (1957), or Chem. Abstracts 57, 7165 1 (1962).

Generally speaking, substitution of the acrylonitrile on the aromatic nucleus follows the normal ortho-para substitution rules known to those skilled in the art with the position para to the OH group being the major point of attachment.

The propionitrile (VI) can be isolated from the reaction mixture after neutralizing the Lewis acid using methods well known in the art, for example, extraction, crystallization, column chromatography, and the like.

Conversely, the crude reaction mixture containing (VI), after it has been neutralized, can be used directly in the next step without further purification. However, it is preferred to isolate (VI) from its reaction mixture in order to obtain optimum yields in the next step.

Cyanoethylation of the phenolic OH of (VI) under O-alkylating conditions to form (VII) is a widely used and well documented process. The phenolic compound is reacted with at least an equimolar amount of acrylonitrile (V), and preferably an excess thereof, in the presence of a basic catalyst at an elevated temperature. Exemplary references which fully describe applicable cyanoethylation procedures are as follows: Organic Reactions Vol. 4, pp 79–135, 1949, John Wiley & Sons, New York, N. Y., J. Chem. Soc. 1945, p 920; Chem. Abstracts 57, 7165 (1962); and U.S. Pat. No. 3,197,434.

The dipropionitrile (VII) is isolated from its reaction mixture using methods well known in the art such as extraction, crystallization and the like. Purified (VII) is not necessary in order to obtain maximum yields in the next step.

When a Scheme B represents the beginning preparative procedure the starting material (IV) is a dihydric phenol and sufficient acrylonitrile (V) is reacted with it under the O-alkylating conditions, using the methods of cyanoethylation referred to hereinbefore, to form the corresponding dipropionitrile derivative (VII) wherein X represents oxygen.

Illustrative of the monohydric and dihydric phenols which can be used in the preparation of the araliphatic diisocyanates of the present invention are phenol, o-cresol, m-cresol, p-cresol, α-naphthol, β-naphthol, hydroquinone, resorcinol, catechol, 1,3-dihydroxynaphthalene, 1,4-dihydroxynaphthalene, 1,5-dihydroxynaphthalene, 2,3-dihydroxynaphthalene, 2,7-dihydroxynaphthalene, 3,3'-dimethyl-4,4'-dihydroxybiphenyl, 2,2-bis(p-hydroxyphenyl)propane, and the like. A preferred group of phenols consists of phenol, hydroquinone, resorcinol, catechol, and 2,2-bis(p-hydroxyphenyl)propane.

Catalytic hydrogenation of (VII) to the diamine (VIII) is

carried out using any of the standard methods of catalytic hydrogenation well known to those skilled in the art; see for example, Catalytic Hydrogenation by R. L. Augustine pp 96–100, 1965 Marcel Dekker, Inc., New York, N. Y., and in particular, see the methods described in CA 57, 7165 (1962) and U.S. Pat. No. 3,197,434.

Finally, phosgenation of the diamine (VIII) provides the araliphatic diisocyanates (I) in accordance with the present invention.

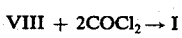

It is well known in the art that aliphatic aminoethers are subject to cleavage under the acidic conditions of phosgenation of the amine to form the isocyanatoether; see U.S. Pat. No. 3,267,122 and Annalen Vol. 562, p 87 (1949). It is therefore quite unexpected to find that the diisocyanates of the present invention can be obtained in high yields by the phosgenation of the aminoalkoxyether intermediates.

The phosgenation is carried out by procedures known in the art. For example, the appropriate diamine, or an acid addition salt thereof such as the dihydrochloride, dihydrobromide, and the like, is treated with phosgene in the presence of an inert organic solvent such as benzene, toluene, xylene, naphthalene, decalin, chlorobenzene, o-dichlorobenzene, bromobenzene, o-chlorotoluene, and the like. The reaction is conducted advantageously at elevated temperatures and preferably at temperatures of the order of 150° to 200° C. The phosgene is conveniently employed in approximately stoichiometric proportions but an excess of phosgene can be employed if desired. In a modification of the above process the appropriate free diamine in an inert organic solvent, as exemplified above, is treated with carbon dioxide to form a salt-like intermediate and then the latter is reacted with phosgene as described above. The above methods of phosgenation are well described and summarized by Siefken, Annalen, 562, 75 et seq., 1949.

The diisocyanates (I) are isolated from the phosgenation reaction product by conventional procedures. For example, the reaction product is purged of excess phosgene using an inert gas such as nitrogen and the inert organic solvent is removed by distillation. The residue is purified by distillation, recrystallization, or like procedures, to give the diisocyanates (I).

Surprisingly, the araliphatic in accordance with the present invention which contain at least one isocyanatoalkylether group (when X represents a single bond), or two isocyanatoalkylether groups (when X represents oxygen), give rise to color stable and ultra violet resistant polyurethanes. As noted in Schollenberger et al, supra, all of the known isocyanates of the prior art which provide polyurethanes having enhanced stabilities compared to aromatic isocyanates, are aliphatic, cycloaliphatic, or araliphatic, which have no additional oxygen present over and above that in the isocyanato function, except those examples wherein aliphatic ester groups are present. It is well known in the elastomer art that aliphatic ether groups are much more susceptible to oxidative type degradation processes than are aliphatic esters; see for example, "Polyether and Polyester Urethane Elastomers-A Comparison", by R. J. Ferrari, Rubber Age, p. 57, par (VII), 1967.

The diisocyanates (I) can be converted to a variety of condensation polymers using procedures well known in the art. Illustratively, the diisocyanates (I) can be converted to polyurethanes, both cellular and non-cellular, using procedures such as those described in Saunders et al, Polyurethanes, Chemistry and Technology, Part II, Interscience, New York, 1964. The polyurethanes so prepared are characterized by markedly increased color stability on exposure to sunlight or ultraviolet irradiation compared with corresponding polyurethanes prepared using aromatic diisocyanates. The polyurethanes so obtained are useful for all the same purposes for which polyurethanes are conventionally employed in the art. For example, the cellular polyurethanes prepared in accordance with the invention can be used for insulation (in the case of rigid compositions) and for mattresses, cushions, upholstery and the like (in the case of the more flexible compositions).

The araliphatic diisocyanates of the present invention can be used in the preparation of light stable elastomeric polyurethanes which are prepared using any of the processes well known in the elastomer art; see Saunders et al., supra, at p 273 et seq. The elastomers so obtained find particular utility in the preparation of coatings, varnishes, films, and decorative products, where color stability is particularly desirable.

The following examples describe the manner and process of making and using the invention and set forth the best mode contemplated by the inventors of carrying out the invention but are not to be construed as limiting.

EXAMPLE 1

1-(3-isocyanatopropoxy)-4-(3-isocyanatopropyl)-benzene a. C-Alkylation of Phenol

A 1 liter flash fitted with a stirrer, thermometer and gas in-let tube was charged with 282 g. (3.0 moles) of phenol and 194 g. (3.6 moles) of acrylonitrile. The stirred mixture was cooled to below 10° C while 200 g. (1.5 moles) of aluminum chloride was slowly added. The temperature was kept below 10° C during the addition. Dry hydrogen chloride gas was bubbled into the stirred mixture for 1.5 hours followed by heating to 80° C during continued hydrogen chloride introduction. A reaction temperature of about 100° to 110° C was maintained for another 2 hours. The flask contents were pured on ice and this mixture stirred until all the aluminum chloride was decomposed. The organic layer was dissolved in toluene which was washed with potassium chloride solution. The toluene solution was dried over anhydrous sodium sulfate followed by concentration to remove solvent. Vacuum distillation of the residue through a vigreux column provided first the unreacted phenol; b.p. (0.1 mm.) at 45° C, followed by a forerun and main cut boiling at 125°–140° C and 139°–140° C, respectively, under 0.1 mm. pressure. Redistillation, without the column, of the combined forerun and main cut provided 167 g. (75% yield), b.p. (0.1 mm.) at 128°–131° C of β-(p-hydroxyphenyl)propionitrile having the formula below.

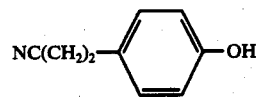

b. O-Alkylation of β-(p-hydroxyphenyl)priopionitrile

A 600 ml. stainless-steel Parr Mini Reactor was charged with 50.0 g. (0.34 mole) of the β-(p-hydroxyphenyl)propionitrile obtained from I(a), 100 ml. acrylonitrile (1.5 moles), 1.0 g. of cuprous chloride and 0.2 g. of potassium t-butoxide. The reactor was flushed with nitrogen and sealed. The reactor contents were heated at about 100° C for 4–5 hours during constant stirring. The reactor was cooled, opened, and the contents concentrated under vacuum. A brownish residue was dissolved in chloroform, extracted 3 times with 5% aqueous sodium hydroxide solution. Evaporation of the solvent provided 46 g. (67% yield) of light yellow-brown crystalline 1-(2-cyanoethoxy)-4-(2-cyanoethyl)-benzene having the formula below

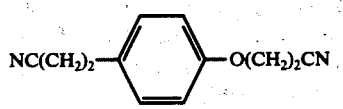

The infrared spectrum was identical with the spectrum of authentic dinitrile.

c. Hydrogenation of the Dinitrile From 1 (b)

A 600 ml. Parr Mini Reactor was charged with 30.0 g. (0.15 mole) of the dinitrile from 1(b) which had been pretreated with charcoal, 250 ml. isopropyl alcohol, 6.0 g. wet Raney-Nickel, and 18 g. of ammonia. The Reactor was pressured to 500 psi of hydrogen. A 1.5 hour period at 150° C and repressuring of the Reactor back to 500 psi under high speed stirring was sufficient to complete the reduction. The reactor was cooled, the contents were filtered to remove solids (catalyst), and the filtrate was concentrated and vacuum distilled to provide 22.8 g. (71% yield) of 1-(3-aminopropoxy)-4-(3-aminopropyl)benzene having the formula below.

d. Phosgenation of the diamine from 1(c)

A 500 ml. flask fitted with a stirrer, thermometer, reflux condenser, and a gas inlet tube was charged with 19.0 g. (0.0675 mole) of the dihydrochloride of the diamine obtained from 1(c) above by bubbling dry hydrogen chloride gas into a methanol solution of the diamine. 250 ml. of o-dichlorobenzene was added to the flask also. The mixture was stirred and heated to 165° C and phosgene passed into the mixture over a period of 1 hour during which time hydrogen chloride was rapidly evolved. The mixture cleared to a solution and an infrared scan of the solution showed the absence of amine function. Solvent was removed under water pump pressure and the residue distilled to provide 1-(3-isocyanatopropoxy)-4-(3-isocyanatopropyl) benzene; b.p. (0.1 mm.) at 165°–169° C; 10.5 g. (60% yield) having the formula below.

EXAMPLE 2

1,3-bis(3-isocyanatopropoxy)benzene a. O-Alkylation of Resorcinol

A 250 ml. flask fitted with a stirrer, thermometer, and reflux condenser, was charged with a mixture of 11 g. (0.1 mole) of resorcinol, 0.5 g. of potassium t-butoxide and 150 ml. (120 g.) of acrylonitrile. The reaction mixture was heated at reflux (80° C) for 25.5 hours. It was then cooled by ice to about 10° C. Filtration of the reaction mixture provided 7 g. (32.4% yield) of the 1,3-bis(2-cyanoethoxy)benzene having the formula below and m.p. 109°–110° C.

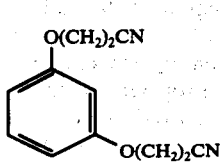

b. Hydrogenation of the dinitrile from 2(a)

A 600 ml. Parr high pressure reactor was charged with 21.6 g. (0.1 mole) of the dinitrile from 1(a), 200 ml. of toluene and 4 g. of Raney Nickel in 50 ml. of toluene. The catalyst had been prewashed 3 times with methanol and 2 times with toluene. After the reactor was sealed and pressurized with 10.5 g (0.62 mole) of ammonia, it was further pressurized to 700 psi of hydrogen. The apparatus was slowly heated to 65° C during stirring whereupon reduction was initiated and these conditions maintained until reduction was complete. The reactor was cooled and catalyst removed by filtration. Evaporation of the filtrate provided 22.55 g. of residue which upon distillation further provided 18.91 g. (84.4% yield), b.p. (0.15 mm.) 158° C, of 1,3-bis(3-aminopropoxy)benzene having the formula below.

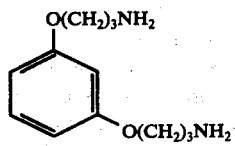

c. Phosgenation of the diamine from 2(b)

A 500 ml. flask fitted with a stirrer, thermometer, reflux condenser, and an addition funnel was charged with a cooled solution consisting of 40 g. (0.404 mole) of phosgene dissolved in 200 ml. of chlorobenzene. A solution consisting of 18.35 g. (0.083 mole) of the diamine 2(b) dissolved in 75 ml. of chlorobenzene was charged to the addition funnel. While the contents of the flask were cooled in ice, and during constant stirring, the diamine solution was added dropwise over a 30 minute period.

Following the addition, the reaction mixture was slowly heated and sparged with phosgene at reflux over a 4 hour period whereupon a clear solution resulted. Excess phosgene was removed by purging with nitrogen. The solution was cooled and concentrated in vacuo yielding a residue which upon distillation provided 18.75 g. (82.2% yield), b.p. (0.1 mm) 178° C, of 1,3-bis(3-isocyanatopropoxy)benzene having the formula below.

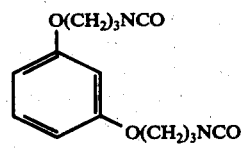

EXAMPLE 3

1,4-bis(3-isocyanatopropoxy)benzene

Using the corresponding procedures and molar amounts set forth in Example 2 but replacing the resorcinol used as starting material by an equivalent amount of hydroquinone there was obtained the following compounds a. 1,4-bis(2-cyanoethoxy)benzene, m.p. 138°–140° C, Yield = 71.7%;
b. 1,4-bis(3-aminopropoxy)benzene, m.p. 73°–74° C, Yield = 90.2%;
c. 1,4-bis(3-isocyanatopropoxy)benzene, m.p. 49°–50° C, Isocyanate equivalent = 139, Yield = 73.3%.

EXAMPLE 4

1,2-bis(3-isocyanatopropoxy)benzene

Using the corresponding procedures and molar amounts set forth in Example 2 but replacing the resorcinol used as starting material by an equivalent amount of catechol there were obtained the following compounds:

a. 1,2-bis(2-cyanoethoxy)benzene, m.p. 124°–125° C, Yield = 22.6%;
b. 1,2-bis(3-aminopropoxy)benzene, b.p. (0.13 mm) 147° C, Yield = 71.2%;
c. 1,2-bis(3-isocyanatopropoxy)benzene, b.p. (0.1 mm) 147° C, Isocyanate equivalent = 139, Yield = 88.9%.

EXAMPLE 5

2,2-bis[p(3-isocyanatopropoxy)phenyl]propane

Using the corresponding procedures, except for the isolation procedures noted below, and molar amounts set forth in Example 2 but replacing the resorcinol used as starting material by an equivalent amount of bisphenol A, there were obtained the following compounds:

a. 2,2-bis[p(2-cyanoethoxy)phenyl]propane, isolated by evaporation of excess acrylonitrile, residue triturated in chloroform and filtered, filtrate washed with 5% caustic solution followed by water wash, dried chloroform solution over magnesium sulfate, removal of chloroform by evaporation followed by recrystallization of the residue from isopropyl alcohol provided 73% yield, m.p. 77°–78° C;
b. 2,2-bis[p(3-aminopropoxy)phenyl]propane, isolated as the dihydrochloride, m.p. 250°–255° C;
c. 2,2-bis[p(3-isocyanatopropoxy)phenyl]propane, non-distillable oil, crude yield = 87%; bis-carbamate derivative from methanol, m.p. 87°–88° C.

EXAMPLE 6

Using the procedures and molar quantities set forth in Example 1, but substituting for the phenol used as starting material the appropriate phenol set forth in Table I there are obtained the corresponding diisocyanates in accordance with the present invention.

TABLE I

| Starting Phenol | Diisocyanate |
|---|---|
| m-cresol | 1-(3-isocyanatopropoxy)-4-(3-isocyanatopropyl)-3-methylbenzene |
| p-cresol | 1-(3-isocyanatopropoxy)-2-(3-isocyanatopropyl)-4-methylbenzene |
| α-naphthol | 1-(3-isocyanatopropoxy)-4-(3-isocyanatopropyl)naphthalene |

EXAMPLE 7

Using the procedures and molar quantities set forth in Example 2 but substituting for the resorcinol there used as starting material, an equivalent amount of the dihydric phenol set forth in Table II there are obtained the corresponding diisocyanates in accordance with the present invention.

TABLE II

| Starting Phenol | Diisocyanate |
|---|---|
| 3,3'-dimethyl-4,4'-dihydroxybiphenyl | 4,4'-bis(3-isocyanatopropoxy)-3,3'-dimethylbiphenyl |
| 1,4-dihydroxynaphthalene | 1,4-bis(3-isocyanatopropoxy)naphthalene |
| 1,5-dihydroxynaphthalene | 1,5-bis(3-isocyanatopropoxy)naphthalene |

EXAMPLE 8

The following example sets forth the preparation of a light stable polyurethane elastomer using an araliphatic diisocyanate in accordance with the present invention.

A 250 ml beaker was charged with a mixture of 16.6 g of Teracol 650 (a tetramethyleneglycol, E.W.=331, supplied by E. I. DuPont Company, Wilmington, Del.), 10.9 g of the araliphatic diisocyanate of Example 3 (E.W.=139), and 1 drop of a catalyst consisting of a 50/50 wt. % mixture of stannous octoate and dioctyl phthalate. The contents of the beaker were thoroughly blended by stirring with a wooden tongue depressor and the beaker then placed in a vacuum oven where heating at about 85° C under approximately 30 mm pressure was continued for 1 hour. A viscous prepolymer was obtained in which the NCO/OH ratio was 1.5.

Into the prepolymer, there was immediately blended 2.5 g of PEHQ[1,4-bis(2-hydroxyethoxy)benzene, E.W.=99, supplied by Eastman Chemical Products, Inc., Kingsport, Tenn.] as a diol extender, which brought the NCO/OH to 1/1. Three drops of the catalyst described above were added and the blended mass was heated in the vacuum oven for 4 hours at 85° C.

A plaque of water-white polyurethane elastomer was removed from the beaker and compression molded at 385° F into a water-white film.

Samples of the film were exposed for 200 hours to direct ultra violet irradiation and 100% relative humidity in a Weather-Ometer apparatus (manufactured by Atlas Electric Devices Co., Chicago, Illinois) in accordance with ASTM Test D750. The samples showed no color change and were classified as light stable.

We claim:
1. An araliphatic diisocyanate having the formula

OCN(CH$_2$)$_3$OArX(CH$_2$)$_3$NCO wherein X is oxygen or a single bond and Ar is an arylene radical selected from the group consisting of phenylene, tolylene, naphthylene, diphenylylene, and radicals having the formula

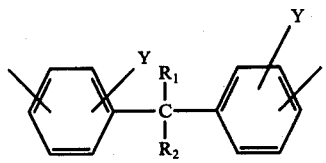

wherein R$_1$ and R$_2$ each represent a moiety selected from the class consisting of hydrogen and alkyl having from 1 to 4 carbon atoms inclusive, and Y is selected from the group consisting of hydrogen, alkyl from 1 to 4 carbon atoms, and alkoxy from 1 to 4 carbon atoms.

2. An araliphatic diisocyanate according to claim 1 wherein Ar is phenylene.

3. An araliphatic diisocyanate having the formula

OCN(CH₂)₃OAr(CH₂)₃NCO wherein Ar is an arylene radical selected from the group consisting of phenylene, tolylene, naphthylene, diphenylylene, and radicals having the formula

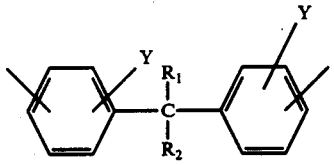

wherein R₁ and R₂ each represent a moiety selected from the class consisting of hydrogen and alkyl having from 1 to 4 carbon atoms inclusive, and Y is selected from the group consisting of hydrogen, alkyl from 1 to 4 carbon atoms, and alkoxy from 1 to 4 carbon atoms.

4. An araliphatic diisocyanate according to claim 3 wherein Ar is para phenylene and said diisocyanate is 1-(3-isocyanatopropoxy)-4-(3-isocyanatopropyl)benzene.

5. An araliphatic diisocyanate having the formula

OCN(CH₂)₃ OArO(CH₂)₃ NCO wherein Ar is an arylene radical selected from the group consisting of phenylene tolylene, naphthylene, diphenylylene, and radicals having the formula

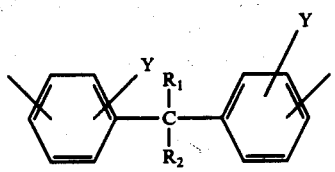

wherein R₁ and R₂ each represent a moiety selected from the class consisting of hydrogen and alkyl having from 1 to 4 carbon atoms inclusive, and Y is selected from the group consisting of hydrogen, alkyl from 1 to 4 carbon atoms, and alkoxy from 1 to 4 carbon atoms.

6. An araliphatic diisocyanate according to claim 5 wherein Ar is para phenylene and said diisocyanate is 1,4-bis(3-isocyanatopropoxy)benzene.

7. An araliphatic diisocyanate according to claim 5 wherein Ar is meta phenylene and said diisocyanate is 1,3-bis(3-isocyanatopropoxy)benzene.

8. An araliphatic diisocyanate according to claim 5 wherein Ar is ortho phenylene and said diisocyanate is 1,2-bis-(3-isocyanatopropoxy)benzene.

9. An araliphatic diisocyanate according to claim 5, wherein Ar is 2,2-bis(p-phenylene)propane and said diisocyanate is 2,2-bis[p-(3-isocyanatopropoxy)phenyl]-propane.

* * * * *